United States Patent
Rinn

(10) Patent No.: US 11,073,457 B2
(45) Date of Patent: Jul. 27, 2021

(54) APPARATUS AND METHOD FOR DETERMINING MATERIAL PROPERTIES OF A MATERIAL

(71) Applicant: Frank Rinn, Heidelberg (DE)

(72) Inventor: Frank Rinn, Heidelberg (DE)

(*) Notice: Subject to any disclaimer, the term of this patent is extended or adjusted under 35 U.S.C. 154(b) by 0 days.

(21) Appl. No.: 16/282,927

(22) Filed: Feb. 22, 2019

(65) Prior Publication Data

US 2019/0265144 A1    Aug. 29, 2019

(30) Foreign Application Priority Data

Feb. 23, 2018  (DE) .................... 10 2018 202 778.1
Feb. 21, 2019  (DE) .................... 10 2019 202 379.7

(51) Int. Cl.
| | |
|---|---|
| *G01N 9/36* | (2006.01) |
| *G01N 27/04* | (2006.01) |
| *G01N 3/42* | (2006.01) |
| *G01N 19/10* | (2006.01) |

(52) U.S. Cl.
CPC ................ *G01N 9/36* (2013.01); *G01N 3/42* (2013.01); *G01N 19/10* (2013.01); *G01N 27/048* (2013.01); *G01N 2203/0003* (2013.01)

(58) Field of Classification Search
CPC .......... G01N 9/36; G01N 27/048; G01N 3/42; G01N 19/10; G01N 2203/0003; G01N 3/48
USPC .... 73/32 R, 73, 866, 81–84, 335.03, 335.04, 73/335.05; 374/100, 142, 183–185; 324/691, 693–724
See application file for complete search history.

(56) References Cited

U.S. PATENT DOCUMENTS

| | | | | |
|---|---|---|---|---|
| 3,491,595 | A * | 1/1970 | Griffeth | G01N 27/046 374/142 |
| 3,968,428 | A * | 7/1976 | Numoto | G01N 27/041 324/694 |
| 6,404,204 | B1* | 6/2002 | Farruggia | G01N 27/06 324/425 |
| 2004/0095154 | A1* | 5/2004 | Lundstrom | G01N 33/246 324/694 |
| 2011/0273196 | A1* | 11/2011 | Hill | A01G 25/167 324/696 |
| 2012/0182016 | A1* | 7/2012 | Ahler | G01V 3/15 324/348 |
| 2013/0241580 | A1* | 9/2013 | Rinn | G01N 27/045 324/693 |
| 2015/0204708 | A1* | 7/2015 | Nichols | G01F 23/24 73/304 R |
| 2018/0292339 | A1* | 10/2018 | Gunzenhauser | A01B 79/005 |
| 2019/0226969 | A1* | 7/2019 | Anderson | G01N 9/36 |

* cited by examiner

*Primary Examiner* — Robert R Raevis
(74) *Attorney, Agent, or Firm* — Jason P. Mueller; FisherBroyles, LLP

(57) ABSTRACT

A device is provided for determining material properties of a material, preferably a wood or a wooden material, having a pin arrangement having at least two pins, a drive unit for at least partially driving the pins into the material using a defined force, and a measuring unit for measuring both the penetration depth of at least one of the at least two pins and also an electrical resistance between two of the pins.

12 Claims, 3 Drawing Sheets

APPARATUS AND METHOD FOR DETERMINING MATERIAL PROPERTIES OF A MATERIAL

CROSS-REFERENCE TO RELATED APPLICATIONS

Figure 1:
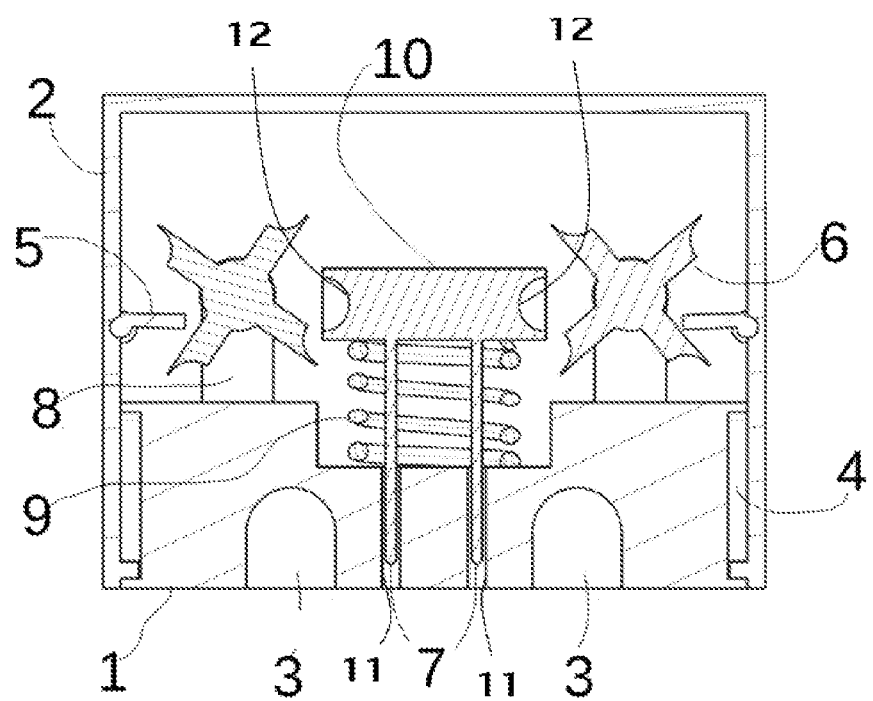

This application claims priority to German Patent Application No. 10 2018 202 778.1, filed Feb. 23, 2018, and also to German Patent Application No. 10 2019 202 379.7, filed Feb. 21, 2019, the entire contents of each of which are incorporated herein by reference.

The disclosure relates to a device for determining material properties of a material, preferably of a wood or a wooden material, having a pin arrangement having at least two pins, a drive unit for at least partially driving the pins into the material using a defined force, and a measuring unit for measuring both a penetration depth of at least one pin and also an electrical resistance—in relation to, for example, direct current, alternating current, and pulsed current—between each two pins.

Furthermore, the present disclosure relates to a method for determining material properties of a material, preferably of a wood or a wooden material, wherein at least two pins of a pin arrangement are driven at least partially into the material by means of a drive unit using a defined force, and wherein a penetration depth of at least one pin and also an electrical resistance—in relation to, for example, direct current, alternating current, and pulsed current—between each two pins and preferably a temperature of at least one pin are all measured by means of a measuring unit.

HILTI AG (Liechtenstein) already described a method in a patent application in the 1960s, in which a steel pin is driven using defined (spring) force into a material, preferably wood, and the density of the material is estimated on the basis of its penetration depth. Up to this point, various devices of several producers have appeared on the market which implement this measuring principle in different ways (inter alia, the "PILODYN"). The use is usually performed by scientists in forestry and wood research and also by experts in forestry (for example, in plantations) and in the timber trade. Because the penetration depth measured in these ways is also dependent on the wood moisture content and temperature, these material properties of the wood are in turn acquired as needed in other ways, i.e., using other measuring units, to be able to correct the density values determined via puncture sample.

At approximately the same time as the puncture density measurement, the determination of the relative wood moisture content via the measurement of the electrical resistance between two metallic pins, which are inserted parallel to one another but generally transversely to the fibers, into the wood, also established itself. Such wood moisture content measuring units have become widespread worldwide in the meantime and are even found in hardware stores for a few euros. While the hardware store variants largely only have short steel tips which only penetrate a few millimeters, to determine the moisture content of firewood, for example, more professional device variants are used more by craftsmen on construction sites to test the moisture content of construction wood using longer drive-in pins. In the devices which are distributed worldwide for experts and scientists (for example, the product HYDROMETTE® having ram-in electrode from GANN), the longer metal pins are pressed step-by-step into the material via swing piston ram sounding, to determine the wood moisture content in the depth of the material, for example, using pins insulated on the shaft. These devices are used in the field of construction site monitoring, particularly because some are also usable on other materials such as stone, plaster, and concrete.

The wood moisture content detected in these ways is dependent not only on the water content of the wood, but rather also on the wood density and (chemical) ingredients, for example, tannic acid and possibly present fungi, some of which degrade wood, i.e., reduce its carrying capacity. Therefore, these methods are also used to establish damage by infestation with wood-destroying fungi in the earliest possible stages. Since this infestation usually only occurs if the wood was sufficiently damp beforehand over a correspondingly long time, the colonization of fungi can sometimes also be prevented after wood moisture content measurements. For this reason as well, wood moisture content measurements are an effective means for construction site upkeep.

In expert and in particular scientific applications, the most accurate results for the wood moisture content are achieved if not only the conductivity but rather also the density of the wood studied and also the temperature are determined and the measured conductivity values are converted, corrected accordingly, into wood moisture content values. Since this can be quite complex depending on the area of application, in particular on location at a construction site, some wood moisture content measuring units enable a manual setting of the air temperature and a selection of the type of wood or type of wood group, for each of which mean density values for correction are then stored in the more or less concealed and electronically coded algorithm.

Interestingly, injuries occur with some regularity with many measuring units for these two applications, for example, by pinching the fingers in the windup device, when triggering the impact pin movement, or by the manual ramming by means of swing piston. These applications are thus heretofore certainly not unproblematic, or even hazardous.

The present disclosure is therefore based on the object of specifying a device and a method for determining material properties of a material, according to which a particularly high accuracy is enabled in the determination of the material properties using simply designed means.

The above object is achieved according to the disclosure by a device having the features of claim 1 and by a method having the features of claim 11.

It has firstly been recognized in an inventive manner that it is not necessary to make use of multiple different devices to measure different parameters. It has then been recognized in a further inventive manner that not only a penetration depth but also an electrical resistance between the pins driven therein can be measured by skillful design of the device. The measuring unit is thus designed both for measuring a penetration depth of at least one pin and also for measuring an electrical resistance between each two pins. Since penetration depth and electrical resistance mutually influence one another depending on the material, the common determination at the same location in the same material enables a higher accuracy of the results, since the values can be mutually corrected and/or compensated.

A particularly high accuracy in the determination of the material properties is therefore enabled using simply designed means using only one combined device by the device according to the disclosure and the method according to the disclosure.

With respect to a further increase of the accuracy in the determination of the material properties, the measuring unit can additionally be designed for measuring a temperature of at least one pin. The temperature also plays a role, for example, in the determination of a moisture of the material in conjunction with the measurement of the electrical resistance and/or the penetration depth. A particularly high accuracy can thus be achieved upon the additional measurement of the temperature by carrying out a skillful correction and/or compensation of measured values.

With respect to a particularly informative measurement, for example, of a conductivity, the pin arrangement can have two pins, each electrically insulated in a region facing toward or facing away from a tip, or two pins each divided along a shaft into electrically isolated segments. An electrical resistance measurement can be performed in defined different penetration depths by an insulation in a region of the shaft facing away from or facing toward a tip. The measurement then takes place in the respective non-insulated region. The pin arrangement can preferably additionally have two pins which are not electrically insulated along a shaft and are not divided into segments. Using such non-insulated pins, a measurement of a conductivity can then additionally be carried out over the complete penetrated length of the pins. A comparison between these different recorded measured values of the conductivity is hereby enabled in a simple manner.

In a further advantageous manner, the pin arrangement can have pins arranged in relation to one another in such a way that the electrical resistance is measurable simultaneously or in succession in two different directions along the material between each two pins, wherein preferably four pins are arranged in a square or rectangle in relation to one another. Such a design can take into consideration the fact that, for example, woods have different electrical conductivities along a fiber direction and in a direction inclined in relation to the fiber direction. A square or rectangular arrangement of the pins in relation to one another enable simple measurements in directions perpendicular to one another.

There are different options with respect to safe driving of the pins into the material. For this purpose, the drive unit can be designed in various ways. For example, the drive unit can have an electrical or magnetic drive or a mechanical spring mechanism—preferably chargeable via turnstile impellers. Such a mechanical spring mechanism offers the option of independence from an electrical supply. This is very practical in particular upon use of the device in the forest or outside. In this case, the spring mechanism can be designed as chargeable by skilled design. A mechanism having turnstile impellers suggests itself for this purpose.

To avoid injuries to a person operating the device, the drive unit can have a locking mechanism, preferably having a locking pin, for preventing an undesired activation of the drive unit. In particular in a design having a locking pin, which is to be actuated or removed before an activation of the device, a high level of safety may be achieved during the operation of the device.

With respect to a use of the device independent of a power network or of batteries, the measuring unit can be associated with a generator, preferably a piezo element, for generating energy from a movement and/or acceleration of the pins for an operation of the measuring unit. In particular an amount of energy sufficient for the operation of the measuring unit and thus carrying out the measurement can be generated by the movement of the pins generated using the drive unit. A suitably dimensioned accumulator can possibly be provided or installed or integrated in the device for storing energy generated in this manner.

To implement a device which can be handled particularly easily and in particular is insensitive and robust during use outside, the pin arrangement and/or the drive unit and/or the measuring unit can be arranged in a housing. Such a housing offers easy grasping of the device and protection of the units and components arranged there in from soiling. Malfunctions can be substantially avoided in this way.

In a particularly practical manner, the housing can be formed at least in regions from a transparent material, preferably from plastic or glass. This enables direct reading of, for example, a penetration depth or position of the pins if a suitable reference unit or scale is arranged in the housing. A separate unit for leading out the measured values in this respect is not necessary.

In a further advantageous manner, the device can be associated with a camera for detecting and/or storing a position of at least one pin and/or the pin arrangement and/or for detecting and/or storing measurement results, wherein the camera is preferably installed in a or the housing or is integrated into a or the housing. Using such a camera, reading of measured values can be carried out in a very simple manner from outside the housing or from inside the housing—depending on the requirement an application. In this case, the camera can have a suitable memory or can be connected to a suitable memory to store the recorded data and process them if necessary and output them in a suitable manner. The camera can be coupled in this case to a suitable processing unit, wherein a mobile terminal or another computer can be used as the processing unit. Furthermore, reading of measured values using the camera can mean, for example, detecting and/or reading a display unit arranged outside or inside the housing in the form of a display screen, for example.

Depending on the application, a density of the material determined from the measured penetration depth and/or a moisture content of the material determined from the measured electrical resistance and/or a measured temperature can be corrected and/or compensated in consideration of at least one of the respective two other measured parameters using the device according to the disclosure or using the method according to the disclosure. This offers a particularly high level of accuracy in the determination of material properties.

Important aspects and advantages of exemplary embodiments of the device according to the disclosure and the method according to the disclosure will be explained hereafter:

A combination of the above-mentioned methods can be carried out in a device and measuring procedure, wherein additional advantages can be achieved depending on the mechanical embodiment in order to avoid the above-mentioned disadvantages: depending on the area of application, two or more pins are driven using defined force into the material to be studied, temperature of the pins stuck in the wood, penetration depth of the pins, and electrical resistance between the pins are then measured at the same time. Because these properties mutually influence one another, the common determination at the same location in the same material enables a higher accuracy of the results because the values can each be mutually corrected.

If the metal pins are not insulated on the shaft, the conductivity in the material is thus detected over the complete penetrated length of the pins, which means good averaging over the space thus detected between the pins, wherein it is possible to convert correctly with respect to the penetration depth measured at the same time, which was not possible in the previous apparatuses. Alternatively, the pins can be divided into electrically isolated segments—similar to a jack plug—so that the conductivity and thus above all the material moisture content can be determined at the same time in different penetration depths.

For examining wood, two pins would usually be theoretically sufficient. However, because the conductivity is also dependent on the fiber direction in the wood, an embodiment of the device having four pins in the square pattern is advantageous, which are in turn arranged on the examination object in such a way that the fibers extend between two pins in the longitudinal direction and between the other two pins in the transverse direction. The overall value determined therefrom is accordingly more precise both for the density and also with respect to the wood moisture content. If two of these pins are embodied as completely conductive and two are segmented or insulated in the shaft, an alternating measurement between different pin pairs enables a correspondingly more accurate characterization of the properties of the material and possible moisture content gradients from the outside to the inside.

In all cases, the device is to be designed so that no injury occurs during use.

The driving in of the pins using defined force can either be performed directly by means of electrical positioning drive, for example, using a servo drive, which also has the advantage that the force changes due to changing of the electrical parameters and the penetration depth can be detected as a function thereof. However, in consideration of the sometimes substantial density of wood and the high application frequency, a correspondingly large accumulator capacity is necessary. The presently most efficient accumulators, in particular lithium-ion accumulators, are in turn sensitive to shock and impact, which requires correspondingly complex protective precautions. These hurdles can be technically overcome, but this increases the costs of the device accordingly.

However, the movable block having pins could also be tensioned against a spring via electrical or magnetic drive, which then ensures the penetration of the pins with defined force. The accumulators can then be better separated mechanically and protected from shocks.

There are now various options for designing and refining the teaching of the present disclosure in an advantageous manner. For this purpose, reference is made, on the one hand, to the following claims and, on the other hand, to the following explanation of a preferred exemplary embodiment of the device according to the disclosure and the method according to the disclosure on the basis of the drawing. Generally preferred designs and refinements of the teaching are also explained in conjunction with the explanation of the preferred exemplary embodiments. In the figures of the drawing FIG. 1 shows a schematic side view in section of an exemplary embodiment of the device according to the disclosure, FIG. 2 shows the exemplary embodiment according to FIG. 1 in different operating states in schematic side views, and FIG. 3 shows a schematic bottom view of a further exemplary embodiment having four pins.

Figure 2:
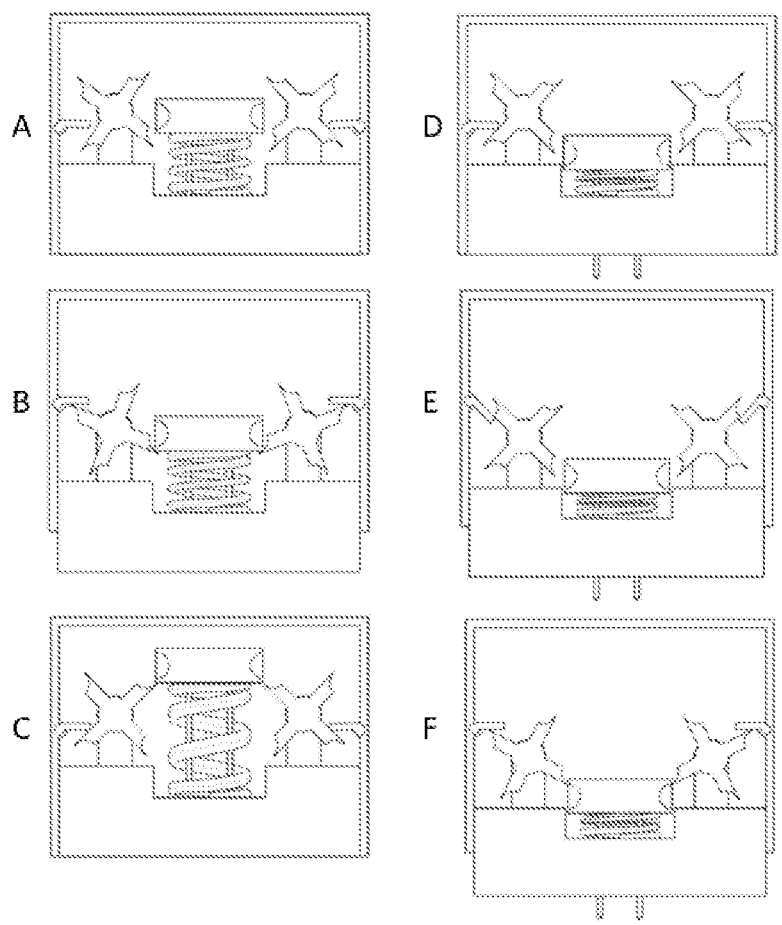
Figure 3:
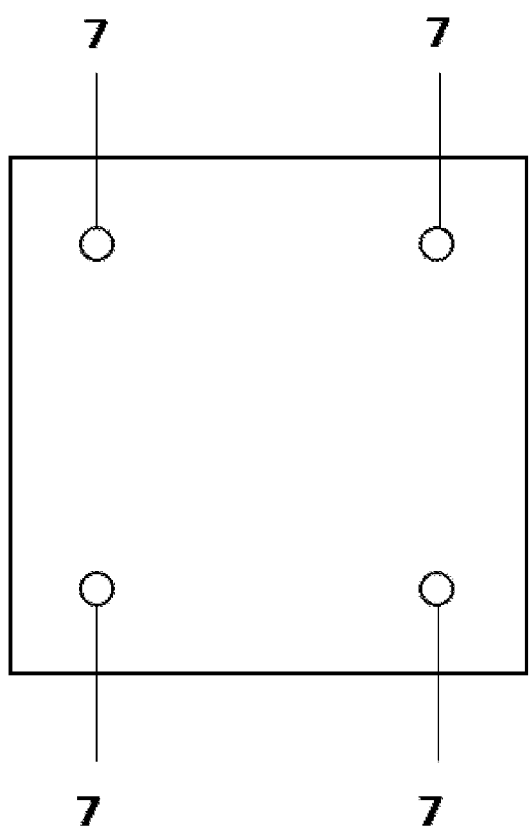

An exemplary embodiment of the device according to the disclosure is shown in schematic side views in each of FIGS. 1 and 2, wherein FIG. 1 shows the device in the idle state and FIG. 2 shows the device in the idle state and in different operating states.

In many areas of application it is not only desired and preferred by the user, but rather also advantageous, due to the sometimes difficult boundary conditions in remote regions of application, for example, in the frost, on wooden bridges, etc., if the device is essentially mechanically driven and also functions without a separate power supply.

For this purpose, a lever, turnstile, and spring structure located completely in the interior of the device can be used, which is designed so that measuring pins 7 only come out of the device when they are placed on a material and the drive spring or springs 9 is tensioned via pressure on a housing 2 or the device. The risk of injury is thus minimized.

In the idle and starting states, the support block 1 is located completely in the surrounding, preferably cup-shaped housing 2. To start a measuring procedure, firstly the support block 1 is drawn downward out of the housing 2. Engagement holes 3 in the support block 1 help in this case, for example. Lateral guide grooves 4 prevent the support block 1 from falling out downward out of the cup housing or housing 2. The idle position of the support block 1 could optionally also be ensured using a locking pin (not shown here), which preferably not only secures or clamps the support block 1 in the housing 2, but rather also the pins 7.

When the support block 1 is drawn downward out of the housing 2, the rockers 5 fastened in the interior on the housing 2 fold in to pass upward by vane arms 6 of a turnstile. Above this, they fold out again. The support block 1 can then be placed in the correct position on the material to be examined. LED lasers (not shown) seated adjacent to the measuring pins 7 can mark the location of measuring points on the surface to be checked, wherein positioning with millimeter accuracy is usually not important—particularly because the dimensions of the entire device are relatively small in any case in consideration of the typical spacings of the measuring pins 7 from one another of a few, preferably approximately 2 to 3 cm. Therefore, the position of the measuring points can already be detected on the basis of the position of the support block 1 on the material and selected accordingly.

After the positioning of the support block 1 on the point to be measured of the material to be examined, the housing cup or the housing 2 is thus pressed downward. Two turnstile brackets 8 each preferably having four vane arms 6 beveled at the tip on one side are preferably seated on the respective turnstile on the support block 1.

In the idle position of the spring 9 tensioned between support block 1 and pin block 10, it holds the pin block 10 at a moderate height. When the outer housing cup or the housing 2 is pressed downward, the rockers 5, which are only tiltable downward, press on the vane arms 6 of the respective turnstile pointing upward toward the outer housing 2, whereby the opposing, lower inner arm raises the pin block 10 upward and thus tensions the spring 9 by an elongation of the spring 9.

As soon the inner lifting turnstile arm or vane arm 6 releases the pin block 10, it is drawn downward by the spring 9 from defined height, so that the measuring pins 7 are pressed with defined force into the material located below the support block 1. The achieved penetration depth of the pins 7 can be read directly on the basis, for example, of the position of the pin block 10 through the preferably transparent housing 2 having, for example, printed scale. Therefore, a separate display does not have to be placed on the outside, as is the case in the devices heretofore found on the market and which makes them more complex and costly.

The length of the measuring pins 7 is preferably selected so that they are not raised upward out of guide holes 11 of the support block 1 even with maximum raising of the pin block 10. Pin length and spring 9 are in turn preferably embodied so that the pins 7 do not protrude downward out of the device in the idle state, i.e., in the idle position of the spring 9, so that there is no risk of injury.

Measurement and Documentation:

When the pins 7 are stuck in the material, the measurements are performed. The penetration depth is readable directly. The measurement of the conductivity between the pins 7 and the temperature of the measuring pins 7 generally only requires fractions of a second. The energy required for this purpose can be taken from a battery or an accumulator.

In the moisture content measuring devices conventional up to this point, the 9 V block batteries typical therein are usually sufficient for several years to execute thousands of measurements and display the respective value. The power consumption for the measurement is thus minimal. The current for these short measurements can therefore also alternatively be generated by a piezo ceramic on the pin block, for example, because the accelerations generated during the hammering in are sufficient for this purpose.

A display for the measured values, for example, conductivity and/or temperature, can be attached on the top of the pin block 10 and read through the housing 2, which is transparent in this exemplary embodiment.

The documentation of the measurement results has heretofore typically been performed in the previously typical single methods in that the values are noted. The position of the measurement is usually additionally documented using a photo.

In the exemplary embodiment described here, in particular the transparent embodiment of the housing 2 enables for the first time the local measuring position and also the measuring results to be documented as a whole and at the same time on one photo, because the measurement results, in particular penetration depth, temperature, and conductivity, are visible at the same time from the outside.

Optionally, an ultrasmall camera, which has become available in miniaturized form in the meantime, and which is attached in the cup housing or housing 2, could even detect and document measurement results and position.

To detach the pins 7 from the material again after the measurement, the housing 2 is firstly drawn upward until the lateral rockers 5 are located above the upper outer turnstile arms or vane arms 6. The cup housing or housing 2 can then again be pressed downward to move the turnstile and thus draw the pin block 10 upward by the two turnstile arms or wing arms 6 pointing inward engaging in a correspondingly formed opening or recess 12 in the pin block 10 and raising it until the pins 7 are detached from the material to be studied. The pin block 10 is then moved by the spring 9 back into the middle starting and idle position and held there.

Sequence of the Work Steps according to FIG. 2:

The device has the smallest dimensions in the idle position A. After the housing 2 is raised according to B, so that the lateral rockers 5 are located above the turnstile vane arms 6, the housing 2 can subsequently be pressed downward according to C in order to raise the pin block 10. The spring 9 is stretched apart at the same time. As soon as the lever arms or vane arms 6 release the pin block 10, it is drawn downward by the spring 9 according to D and penetrates into the material to be studied in consideration of defined force as deeply as the density of the material permits. It was already shown in the nineteen sixties by HILTI AG that the penetration depth of such pins 7—often simple steel nails are used—correlates with the density of the material at defined hammering force, and this was later one of the starting points of diverse diagnostic techniques for woods, inter alia, the needle drilling resistance measurement. To be able to draw the pins 7 stuck in the material to be studied back out of the material, the housing 2 is raised again according to E, wherein the lateral rockers 5 fold in to pass by the turnstile vane arms 6. The pin block 10 can then be raised again according to F by again pressing down the upper cup housing or housing 2, because the turnstile vane arms 6 engage laterally in the pin block 10 and can move it upward.

FIG. 3 shows a further exemplary embodiment of the device according to the disclosure, wherein FIG. 3 is a bottom view which shows that the device of this exemplary embodiment has four pins 7 in a square arrangement.

Advantages of this Procedure and this Device Over the Heretofore Typical Single Methods:

- Combination of penetration depth, conductivity, and temperature measurement
    - higher accuracy of the measurement results
    - many times faster measurement of the material properties
- two, three, four, or more pins 7 for simultaneous measurements
    - higher accuracy and significance of the measurement results
- mixture of pins 7 insulated on the shaft and fully-conductive pins
    - higher accuracy of the measurement results
- The determination of the penetration depth of the non-insulated pins 7 enables the calibration of the measured conductivity value to the active length (=penetration depth).
- closed housing 2 and measurement procedure without risk of injury
    - measurement can occur, and therefore the pins 7 can protrude from the housing 2, only when the device is placed, the cup housing or housing 2 is unlocked and actively pressed down
- transparent housing 2
    - saves feeding measured items of information outward and corresponding separate displays
    - enables the simultaneous documentation of measuring position and all measurement results using one photo
    - enables the visual check of the measuring procedure and the recognition of possible technical problems In one exemplary embodiment of the device according to the disclosure, it can be a penetration pin combination measuring device and a method for mutually corrected and temperature-compensated determination of various material properties, such as density and moisture content in particular, preferably on wood and wooden materials, wherein two or more pins 7 are pressed using defined force into the material to be studied and penetration depth, conductivity, and temperature can be measured at the same time, so that they can be mutually corrected and/or compensated.

By combination of, for example, two pins electrically insulated on the shaft of the pin 7 and two pins 7 not insulated on the shaft, both mean moisture values and also those in deeper layers can be detected at the same time.

By combination of, for example, four identical pins 7 in a square arrangement, conductivities can be detected at the same time parallel and perpendicular to the wood fibers or other directions, which are preferably orthogonal to one another.

The pins 7 can be pressed into the material by an internal spring mechanism charged via turnstile impellers.

For example, for safety reasons, the spring raising mechanism can only function when a locking pin is removed, the device is placed on a material after pulling out the support block 1, the housing 2 is firstly drawn upward and then pressed downward to tension the spring 9 until the pins 7 are released after release by the turnstile impellers and can be drawn downward by the spring 9 to penetrate into the material located in front of the support block 1.

The housing 2 can be embodied from transparent material to read and photographically document all relevant measurement results at the same time and also be able to check the functionality of the device.

The current for the measurement can be generated by a piezo element from the acceleration during the raising and lowering of the pins 7.

An installed camera can document and also store the position and measurement results.

Reference is made to the general part of the description and to the appended claims with respect to further advantageous embodiments of the device according to the disclosure and the method according to the disclosure to avoid repetitions.

Finally, it is to be expressly noted that the above-described exemplary embodiments are only used to explain the claimed teaching, but do not restrict it to the exemplary embodiment.

LIST OF REFERENCE NUMERALS 1 support block
2 housing
3 engagement hole
4 guide groove
5 rocker
6 vane arm
7 measuring pin, pin
8 turnstile bracket
9 spring
10 pin block
11 guide hole
12 recess

The invention claimed is:

1. A device configured to determine material properties of a material, the device comprising:
   a housing;
   a pin arrangement having at least two pins supported by the housing;
   a drive device supported by the housing and configured to at least partially drive the at least two pins into the material using a defined force,
   a position measurement device supported by the housing, the position measuring device configured to measure a penetration depth of the at least two pins; and
   an electrical measurement device, the electrical measurement device configured to measure an electrical resistance between each of the at least two pins.

2. The device as claimed in claim 1, wherein the device further comprises a temperature measurement device configured to measure a temperature of at least one of the at least two pins.

3. The device as claimed in claim 1, wherein the at least two pins includes two pins that are each electrically insulated in a region of a shaft facing away from or toward a tip, or that are each divided along the shaft into electrically isolated segments.

4. The device as claimed in claim 3, wherein the pin arrangement further includes two pins that are not electrically insulated along a shaft and not divided into segments.

5. The device as claimed in claim 1, wherein the at least two pins further comprise four pins that are arranged such that the electrical resistance is measurable simultaneously or in succession in two different directions along the material.

6. The device as claimed in claim 5, wherein the four pins are arranged in a square or rectangle in relation to one another.

7. The device as claimed in claim 1, wherein the drive device has a spring mechanism that is chargeable via turnstile impellers.

8. The device as claimed in claim 1, further comprising:
   a support block configured to removably surround the pins to thereby safely secure the pins when the device for determining material properties of a material is not in use; and
   a locking mechanism configured to prevent an undesired activation of the drive device by securing the support block within the housing.

9. The device as claimed in claim 1, wherein the device further comprises a generator that includes a piezo element configured to generate energy from a movement or acceleration of the at least two pins, the generated energy being provided to the device for operation of the device.

10. The device as claimed in claim 1, wherein the electrical measurement device is supported by the housing.

11. The device as claimed in claim 10, wherein the housing includes regions formed from a transparent material that includes plastic or glass.

12. The device as claimed in claim 1, wherein the device is associated with a camera for detecting or storing a position of at least one of the at least two pins or the pin arrangement, or for detecting or storing measurement results, and wherein the camera is installed in or integrated into a housing.

* * * * *